US005763262A

United States Patent [19]
Wong et al.

[11] Patent Number: 5,763,262
[45] Date of Patent: Jun. 9, 1998

[54] IMMUNODIAGNOSTIC DEVICE

[75] Inventors: Siu-Yin Wong; Fon-Chiu Mia Chen, both of San Diego; Eugene Fan, La Jolla, all of Calif.

[73] Assignee: Quidel Corporation, San Diego, Calif.

[21] Appl. No.: 863,397

[22] Filed: Apr. 3, 1992

Related U.S. Application Data

[63] Continuation of Ser. No. 528,050, Jun. 24, 1990, abandoned, which is a continuation of Ser. No. 909,020, Sep. 18, 1986, abandoned.

[51] Int. Cl.$^6$ .................... C12M 1/00; G01N 33/53; G01N 15/06; C09K 15/32
[52] U.S. Cl. .................... 435/287.2; 435/7.1; 435/287.7; 435/288.2; 422/68.1; 422/69; 422/50; 422/55; 106/310; 252/400; 252/405
[58] Field of Search .................... 436/518; 435/287, 435/283.1, 287.1, 287.2, 287.7, 288.2, 7.1; 422/292, 68.1, 69, 50, 55, 99; 106/310; 252/400, 405

[56] References Cited

U.S. PATENT DOCUMENTS

| | | | |
|---|---|---|---|
| 3,281,860 | 10/1966 | Adams et al. | 239/4 |
| 3,615,222 | 10/1971 | Mead . | |
| 3,645,687 | 2/1972 | Nerenberg . | |
| 3,691,017 | 9/1972 | Brown et al. . | |
| 3,715,192 | 2/1973 | Wenz et al. . | |
| 3,775,058 | 11/1973 | Bush . | |
| 3,811,840 | 5/1974 | Bauer et al. . | |
| 3,843,324 | 10/1974 | Edelman et al. . | |

(List continued on next page.)

FOREIGN PATENT DOCUMENTS

| | | |
|---|---|---|
| 0034049 | 8/1981 | European Pat. Off. . |
| 0051213 | 10/1981 | European Pat. Off. . |
| 0097952 | 1/1984 | European Pat. Off. . |
| 0186100 | 7/1986 | European Pat. Off. . |
| 0217403 | 4/1987 | European Pat. Off. . |
| 0323605 | 7/1989 | European Pat. Off. . |
| 0017358 | 8/1983 | Japan . |
| 2204398 | 4/1988 | United Kingdom . |
| 8404171 | 10/1984 | WIPO . |
| 8505451 | 12/1985 | WIPO . |
| 8702774 | 5/1987 | WIPO . |

OTHER PUBLICATIONS

Zuk, et al., *Clin Chem. 31/7,* 1114–1150 (1985).
Chen, et al., *Clin. Chem. 30/9,* 1446–1451 (1984).
Chandler, et al., *J. of Immun. Meth.* 53: 187–194 (1982).
Valkirs and Barton, *Clin. Chem. 31,* 1427–1432 (1985).
Weinheim, vol. *IV Enzymes 2, Esterases, Glycosidases, Lyases, Ligases.*
Iman and Hornby, *Biochem. Jnl. 129:* 255 (1972).
Campbell, et al., *Biochem. Biophys. ACTA* 384: 307 (1975).
Mattison and Nilsson, *FEBS Letters* 104: 78 (1977).
O'Sullivan and Marks, *Methods in Enzymol.* 73: 147 (1981).
Nakane and Kanaoi, *Jnl. of Histol. and Cytochem.* 82: 1084 (1974).
Neuberger, et al., *Nature* 132: 604 (1984).

*Primary Examiner*—Bradley L. Sisson
*Attorney, Agent, or Firm*—Knobbe, Martens, Olson & Bear

[57] ABSTRACT

A device for assaying biological fluids for molecules contained therein comprising a container, material situated in the container for absorbing fluid and in communication with an antibody or antigen impregnated matrix, wherein the matrix is accessible to the exterior of the container through a funnel shaped aperture in the roof of the container. Further features include a chemical drying agent associated with the container for absorbing moisture, thereby preventing inactivation of the assay reagents, and a filter situated above the antibody or antigen impregnated matrix, and in communication with the matrix through the aperture in the roof of the container. The filter removes interfering substances present in the biological fluids and provides protein blocking agents to the matrix material for decreasing the background of the assay.

1 Claim, 1 Drawing Sheet

U.S. PATENT DOCUMENTS

| | | | |
|---|---|---|---|
| 3,860,003 | 1/1975 | Buell . | |
| 3,888,629 | 6/1975 | Bagshawe | 422/292 |
| 3,979,509 | 9/1976 | Giaever . | |
| 3,990,849 | 11/1976 | Lee et al. . | |
| 4,009,435 | 2/1977 | Hogg . | |
| 4,061,468 | 12/1977 | Lange et al. . | |
| 4,081,301 | 3/1978 | Buell . | |
| 4,094,647 | 6/1978 | Deutsch et al. . | |
| 4,121,222 | 10/1978 | Diebold et al. . | |
| 4,153,675 | 5/1979 | Kleinerman . | |
| 4,168,416 | 9/1979 | Grubb et al. . | |
| 4,200,690 | 4/1980 | Root et al. . | |
| 4,208,187 | 6/1980 | Givner . | |
| 4,235,601 | 11/1980 | Deutsch et al. . | |
| 4,243,694 | 1/1981 | Mansukhani . | |
| 4,246,339 | 1/1981 | Cole et al. . | |
| 4,277,560 | 7/1981 | Gray et al. . | |
| 4,361,647 | 11/1982 | Remington et al. | 435/7 |
| 4,363,874 | 12/1982 | Greenquist . | |
| 4,366,241 | 12/1982 | Tom et al. . | |
| 4,376,110 | 3/1983 | David et al. . | |
| 4,381,342 | 4/1983 | Van Heyningen . | |
| 4,388,343 | 6/1983 | Voss et al. . | |
| 4,391,904 | 7/1983 | Litman et al. . | |
| 4,407,943 | 10/1983 | Cole et al. . | |
| 4,425,438 | 1/1984 | Bauman et al. . | |
| 4,442,204 | 4/1984 | Greenquist et al. . | |
| 4,446,232 | 5/1984 | Liotta . | |
| 4,447,529 | 5/1984 | Greenquist et al. . | |
| 4,461,829 | 7/1984 | Greenquist . | |
| 4,472,498 | 9/1984 | Masuda et al. . | |
| 4,474,878 | 10/1984 | Halbert et al. . | |
| 4,496,654 | 1/1985 | Katz et al. . | |
| 4,497,899 | 2/1985 | Armstrong et al. . | |
| 4,515,595 | 5/1985 | Kievit et al. . | |
| 4,533,629 | 8/1985 | Litman et al. . | |
| 4,582,792 | 4/1986 | Kasahars et al. . | |
| 4,590,157 | 5/1986 | Chandler et al. . | |
| 4,595,661 | 6/1986 | Cragle et al. . | |
| 4,623,461 | 11/1986 | Hossom et al. . | |
| 4,632,901 | 12/1986 | Valkirs et al. . | |
| 4,642,285 | 2/1987 | Halbert et al. . | |
| 4,649,121 | 3/1987 | Ismail et al. . | |
| 4,672,024 | 6/1987 | Giaever et al. . | |
| 4,703,017 | 10/1987 | Campbell et al. . | |
| 4,740,468 | 4/1988 | Weng et al. . | |
| 4,748,042 | 5/1988 | Linnecke et al. . | |
| 4,855,240 | 8/1989 | Rosenstein et al. . | |
| 4,912,034 | 3/1990 | Kalra et al. . | |
| 5,035,704 | 7/1991 | Lambert et al. | 606/182 |
| 5,035,805 | 7/1991 | Freeman et al. | 210/689 |

IMMUNODIAGNOSTIC DEVICE

This application is a continuation of application Ser. No. 528,050, filed Jun. 25, 1990 now abandoned, which is a continuation of Ser. No. 909,020, filed Sep. 18, 1986 now abandoned.

BACKGROUND OF THE INVENTION

The device and methodology described herein facilitates diagnostic assays involving the formation and detection of particulate complexes, particularly immune complexes, which, are difficult or impractical to perform. Traditional methods of testing for particulate complexes are time-consuming and costly, primarily due to the repetitive steps required to carry out the assay, as well as the complexity of the laboratory equipment needed to accomplish it. Further, such tests often necessitate intermediate extraction and washing steps to eliminate interfering substances present in the sample.

A key goal in developing immunodiagnostic test systems is to reduce the time it takes for the user to complete the assay. Consequently, considerable effort has been expended towards reducing the number of steps required to carry out the assay, with the ultimate goal of having a single step assay. The latter presently does not exist.

In addition to decreasing the time it takes to perform the diagnostic test, another desirable property of such systems is that they be stable at room temperature for prolonged periods of time. Generally, diagnostic devices comprise several reagents having different temperature stabilities. Some of these reagents are stable at room temperature for short periods of time, while others are even less stable, or not stable at all. The effect of temperature on the reagents decreases the sensitivity, and reliability of the assay, and increases the background. Most commercial diagnostic devices presently available require that one or more of the reagents used to effect the assay be kept at low temperature to ensure its stability. Indeed, table 1 shows that either the entire diagnostic kits, or the reagents present in the kit, of the three major suppliers that produce hormone pregnancy kits, must be stored at low temperature to be effective. Thus, a diagnostic test system that is room temperature stable for long periods of time would have a clear advantage over state of the art devices.

Most diagnostic devices presently in use are premised on the "sandwich" assay. Here, the analyte, or substance sought to be assayed, is incubated with an excess of antibody molecules bound to solid matrix material. Subsequently, a labeled second antibody, also in excess, but directed against a second determinate on the analyte is incubated with the immune complex formed from the first antibody attached to the solid matrix material. The presence of labeled antibody on the surface of the immune complex is determined by suitable means depending on the type of label used. This type of assay is commonly referred to as a "sandwich", or "2-site" assay, since the antigen has two antibodies bound at two different regions, or epitopes.

A number of "sandwich" assays have been patented (see, for example, U.S. Pat. No. 4,361,647, or 4,497i,899). Despite their widespread use, their performance is not without difficulty. As alluded to above, they require successive manipulations, and suffer from low sensitivity. For instance, a generally used procedure for conducting an immunoassay using the "sandwich" technique involves:

1. Determining the working dilutions of the antibody;
2. Removing any excess antibody used to sensitize the solid matrix material;
3. Washing the solid support matrix free of unbound antibody;
4. Contacting the matrix with the test assay solution;
5. Incubating for extended periods of time the analyte to be detected in the test assay sample so as to allow the analyte to bind to the antibody;
6. Washing the matrix to remove any unreacted material;
7. Contacting the matrix with labeled second antibody;
8. Washing the solid matrix material to remove any unreacted second antibody;
9. Determining the presence of the immuno complex, either directly if the second antibody is radio labeled using suitable counting techniques, or if the label is an enzymatic label by adding a substrate that yields a detectable color change upon reaction.
10. In the instance where the second antibody carries an enzymatic label, after a period of time to allow sufficient color intensity to develop, the reaction is stopped with strong alkaline, or acid.

In addition to being time-consuming and relatively insensitive, "sandwich" assays are further limited in two other respects; first they are not readily adaptable for use with devices to detect more than one antigenic substance present in a sample. Thus, if one wishes to test a sample for multiple antigens, separate aliquots of the sample must be assayed independently. Second, they often make inefficient use of assay sample, thereby necessitating having to assay large sample volumes to obtain a reliable result.

In part this is because the sample is deposited over a large surface area of solid matrix material. Thus, a device premised on the sandwich technique that facilitate assaying multiple antigens, and that makes more efficient use of sample fluid would be a clear advance over state of the art devices.

As alluded to above, an appealing feature presently lacking in diagnostic devices is long term room temperature stability. At present all the reasons for instability have not been identified. However, it appears that part of the cause is due to instability of antibody bound to the solid support matrix, and the formation of aggregates in the antibody-enzyme conjugate employed to detect the presence of antigen. The former problem has not been satisfactory dealt with while the formation of aggregates can be controlled by storing the conjugate at temperatures in the range of two to eight degrees centigrade. At these temperatures the rate of aggregate formation is reduced. However, because it is inconvenient, and expensive to store the diagnostic device at low temperature, considerable effort has been expended to develop antibody-enzyme conjugates that are stable at room temperatures, or methods to reduce the background arising from the aggregates. To date these efforts have been unsuccessful.

Another concern in performing diagnostic assays is to separate immunoreactants that do not bind antigen, and thus do not form part of the immune complex, from bound reactants that form the complex. The presence of unbound reactants can increase the background of the assay. While washing the immune complex can, and, indeed, does remove most of the background signal due to unbound reactants, most assays employ what is termed a blocking step to further reduce the background. The blocking step involves coating the solid support with proteinaceous substances after it has been coated with antibody. The blocking material binds to sites on the solid matrix material which are not covered with antibody, and thus prevents subsequent nonspecific binding of immune reactants that are not part of the immune complex. Generally, the blocking step is performed either before the assay is conducted, hence, necessitating an additional time consuming step, or else, as described in U.S. Pat. No. 3,888,629, the solid matrix material is impregnated with the blocking agent, and then freeze dried and maintained in this state prior to use. The inconvenience in having to pretreat the solid surface with blocking material, or using freeze dried filters, with blocking proteins contained therein, is tedious, time-consuming, and costly. Thus, a method that avoids both of these procedures would yield a more desirable diagnostic device.

In light of the above, it is apparent that while there exists many immunodiagnostic devices, it is desirable to increase their sensitivity, ease and speed of performance as well as their long term room temperature stability.

SUMMARY OF THE INVENTION

An immunodiagnostic assay device is described that has considerable advantages over present state of the art devices, and can be used to perform both sandwich and nonsandwich assays. It has several features that in combination yield a device that is stable at room temperature for long times, yields results quickly, is highly sensitive and, moreover is capable of simultaneously detecting more than one antigen present in the same assay solution.

It will be appreciated by those skilled in the art that while the diagnostic assay device described herein is anticipated to be primarily employed in assaying either antigens or antibodies through the formation of an immune complex, that in fact, its applicability is considerably broader, and is not restricted to these molecules. At a minimum, the device merely requires a first molecule that recognizes and binds a second molecule. The first molecule can be conveniently termed a ligand-recognition molecule, and the latter a ligand. While antibody and antigen are preferred embodiments of a ligand-recognition molecule and ligand respectively the device can be used with a variety of ligands and ligand-recognition molecules. For example, hormone receptor molecules are a type of ligand recognition molecule and can be attached to the solid matrix material, and used to assay for the corresponding hormone ligand. Alternatively, a hormone could be bound to the matrix material and used to assay for hormone receptors. It will be apparent to those skilled in the art that there are many such combinations of ligand-recognition molecules and ligands suitably employable in the present immunodiagnostic device.

If either a sandwich or nonsandwich assay is employed in the present device, a matrix material is impregnated with antibody using a novel printer-coder technique comprising applying one or more distinct antibodies to the matrix by spraying them directly onto it. Using this technique, it is possible to rapidly deposit antibodies in discrete circles, lines, or other geometric shapes for binding one or more antigens. Thus, the number of antigens that can be assayed is a function of the number of different antibodies that can be applied in distinct patterns.

Beneath the antibody impregnated matrix material are two discrete layers of absorbent materials. Directly beneath the matrix material is a mid-layer of material that decreases the background. Further removed from the matrix material is the second layer of absorbent material. Its function is to absorb and hold assay or wash fluids, and can be composed of a wide variety of absorbent materials.

Another aspect of the invention described herein that reduces background activity is a prefilter impregnated with suitable blocking material, particularly, but not exclusively, proteinaceous material. The prefilter is situated over the matrix material, and is impregnated with blocking material by contacting the filter under defined conditions with proteinaceous material. When the assay is performed, a suitable amount of assay fluid is applied to the prefilter which passes through the prefilter carrying the blocking material with it. The assay fluid, and the blocking materials contained therein contact the antibody impregnated matrix material wherein the blocking material binds to nonspecific reactive sites on the matrix material, thereby making these sites unavailable for binding by excess immunochemicals involved in effecting the assay.

An additional feature of the subject invention that contributes to its sensitivity, and long term room temperature stability, is that it can be carried out in a chamber having at least two compartments. One compartment contains the antibody impregnated matrix material, while the second compartment can contain moisture absorbent chemicals. The latter communicates with the former, and enhances the sensitivity and reliability of the assay since it maintains a desiccant like environment in the first compartment. This favorably maintains the stability of the blocking agent in the prefilter, and the antibody associated with the matrix material during prolonged periods of nonuse. The same effect can be realized, albeit not as conveniently by associating the moisture absorbent chemicals with the prefilter and matrix material by other means.

A further feature associated with the present invention is a funnel shaped aperture in the roof of the device that provides access of assay fluid to the matrix material. This design makes efficient use of assay sample, and subsequent washes, by depositing them over a small surface area of matrix material.

It will be understood by those skilled in the art that while the immunodiagnostic device has been described in terms of assaying for antigen by binding antibody to the matrix material, that it's usefulness is not so limited. It will be appreciated that it is suitably employed to assay for antibodies present in assay fluids by attaching their corresponding antigens to the matrix material. This aspect of the invention may aid the detection and diagnosis of autoimmune diseases.

The combination of features associated with the diagnostic device described herein yields a system that is more sensitive than those presently in use, is reliable, convenient to use, has broad applicability, and, moreover, can be stored at room temperatures for long periods of time without loss of activity.

DETAILED DESCRIPTION OF THE INVENTION

It will be apparent to those skilled in the art that the essence of the present invention is a filter impregnated with blocking agent, matrix material suitably impregnated with antibody an absorbent layer for removing excess fluids, and a container for supporting and associating all the above to effect an immunoassay. Thus, while the invention is described below in considerable detail, this description represents the preferred embodiment of the invention, and should not be construed as limiting the invention.

Figure 1:
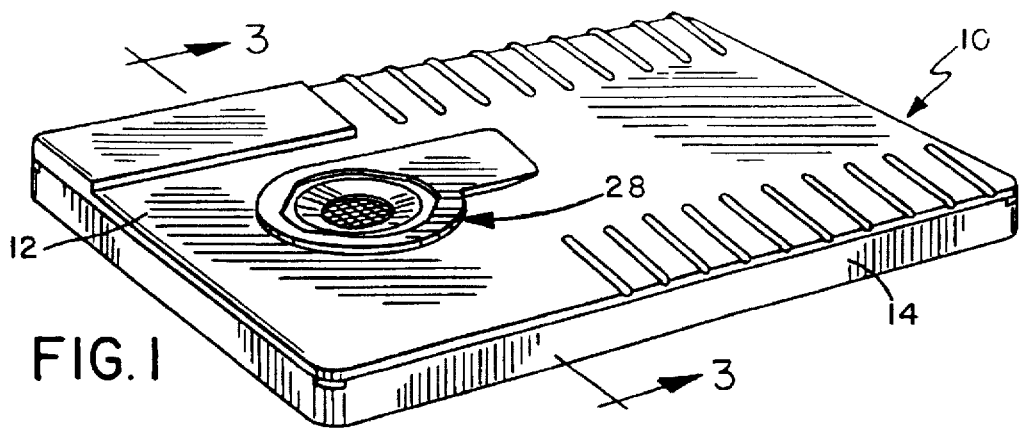
FIG. 1 is a perspective view of the diagnostic unit.
Figure 2:
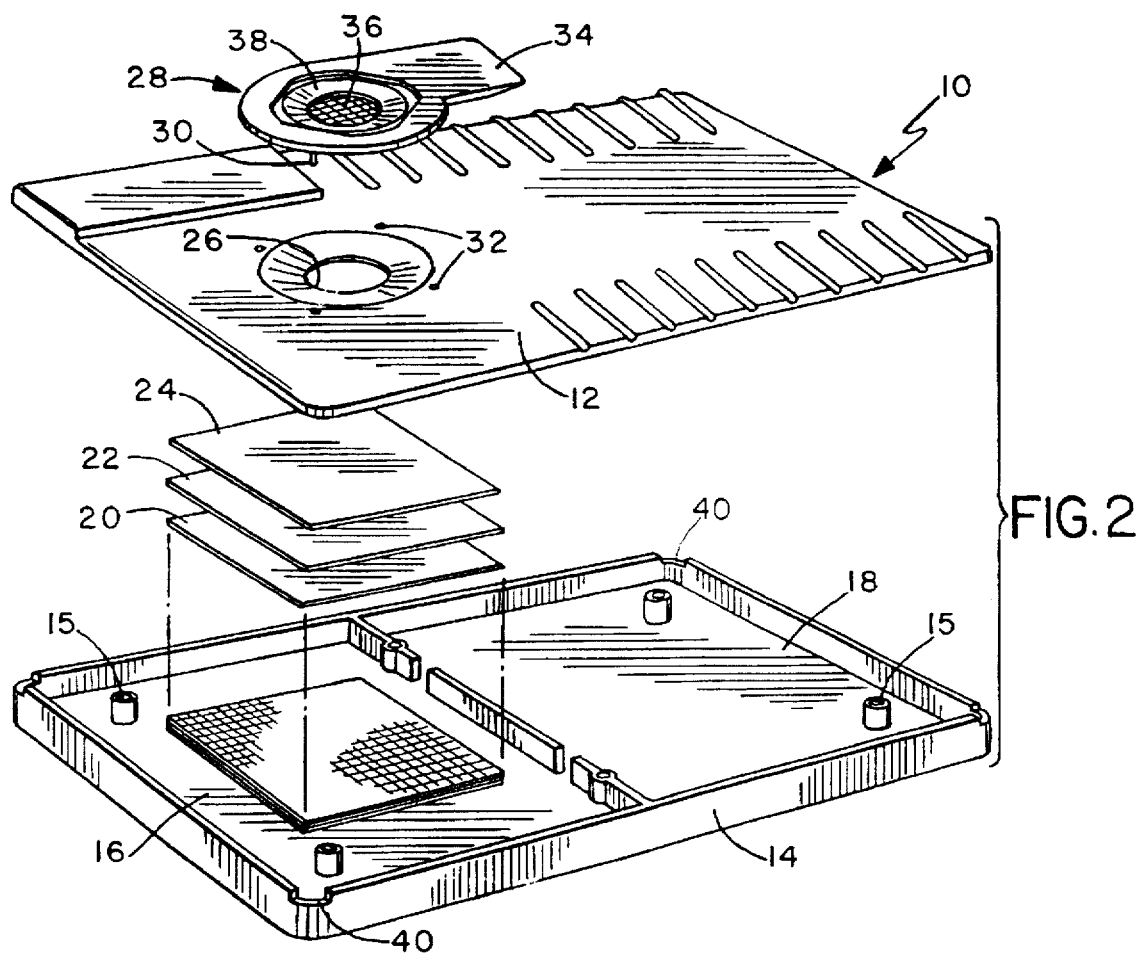
FIG. 2 is an exploded view showing the various components.

FIGS. 1 & 2 show a representative example of a suitable immunodiagnostic test device useable in the present invention. FIG. 1 shows a fully assembled, and FIG. 2 an exploded view of the device. As shown in FIG. 1, it comprises a container 10, having a separable top section 12, and a bottom section 14 and a filtering device 28. FIG. 2 further reveals the container 10 and the top 12 and bottom sections 14. In a preferred embodiment of the invention the bottom section 14 is separated into two chambers 16 and 18. Situated in chamber 16 is absorbent material 20 that receives fluid from the mid-layer 22. The mid-layer 22 in turn receives fluid from matrix material 24. Also shown in FIG. 2 are notches 40 that act as vents for pressure equilibration when the top 12 and bottom sections 14 are joined. The latter reduce the time it takes to perform the assay, but are not essential to carrying out the assay.

The top section 12 of the container 10 has an aperture 26 contained therein. When the top section 12 is aligned with the bottom section 14, by posts 13 affixed to the top section that fit into holes 15 in the bottom section, the aperture is positioned over the matrix material 24. Further, the top section 12 has associated with it a filtering device 28. The filtering device 28 is situated over the aperture 26 such that when fluid is applied to the filtering device 28, the filtrate passes through the aperture 26 and contacts the matrix material 24. The filtering device 28 is associated with the top section 12 by any one of a number of means. It is convenient to accomplish this by having post 30 at the corners of the device 28 fit into receptacles 32 situated on the top section 12.

Both the aperture 26 and the filtering device 28 preferably have a funnel shape configuration. This permits a large amount of sample fluid to be passed through a small amount of surface area of the matrix material 24. While the dimensions of both the aperture 26 and the filtering device 28 can be varied considerably without affecting the performance of the device, we have found the following approximate dimensions to be satisfactory; 1.0 cm bottom diameter, 2.0 cm top diameter, and 0.3 cm deep.

A feature of the subject invention which allows for long term storage without deterioration of the reagents present in the filtering device 28, or the matrix material 24, is a moisture absorbing chemical situated in the chamber 18. Such chemicals prevent moisture from contacting the reagents and causing a loss in activity. A variety of chemicals well known to those skilled in the art are useful for this purpose. It should be apparent that the effectiveness of the present invention is not absolutely reliant on a device having a chamber 18 for holding moisture absorbing chemicals. A single chamber will perform adequately provided the chemicals are otherwise associated with it, for example by disposing them on the outside.

Figure 3:
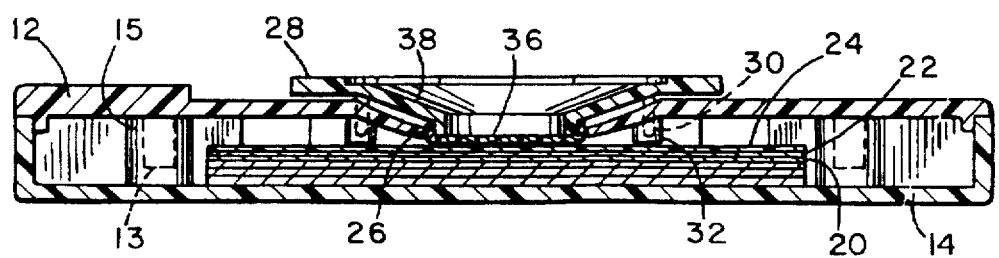
FIG. 3 is an enlarged sectional view taken on line 3—3 of FIG. 1.

FIG. 3 shows an enlarged sectional view of the present invention. The filtering device 28 is affixed to the top section 12 by posts 30 that are situated in holes 32. The top section 12 and bottom section 14 are also joined by posts 13 situated in the top section that fit into holes 15 in the bottom section.

It will be appreciated by those skilled in the art that while the container that forms the diagnostic device shown in FIGS. 1–3 has a flat configuration, that the invention is not limited to this shape. Virtually, any shape will perform adequately provided it has associated with it the elements described above.

The present diagnostic device is useful for detecting a ligand-ligand recognition molecule complex on a solid surface. It is important to note that either the ligand, or the ligand-recognition molecule can be bound to the matrix material 24, and be used to detect the corresponding member of the complex. That is, if the ligand-recognition molecule is bound to the matrix material, then generally, the ligand can be assayed; however, if the ligand is bound to the matrix material 24, then the ligand-recognition molecule can be assayed.

Ligands are generally, but not necessarily small molecular weight molecules such as drugs, peptide hormones, and other bioactive molecules. Ligand-recognition molecules, on the other hand, are generally, but also not necessarily, large molecular weight molecules being most often protein, particularly antibody molecules. Thus, it will be understood by those skilled in the art, that while the subject diagnostic device preferred embodiment is naked antigen and antibody (mono or polyclonal), as ligand and ligand-recognition molecule respectively the invention is not limited to the use of this pair of ligand and ligand-recognition molecules. However, because these are most often used in diagnostic assay procedures, the invention will be described with reference to them.

The diagnostic device described herein will most often be used to detect a "sandwich" immune complex formed of antibody and antigen, and thus will employ a support material as the matrix 24 suitable for binding a nonlabeled first antibody. It will be appreciated however, that the device is equally capable of being used to perform nonsandwich assays, particularly competitive binding assays. The latter are often employed to assay small molecular weight molecules that either have a single antibody binding site, or, because of their size, prevent more than one antibody from binding due to steric hindrance. Thus, the invention can be used to assay drugs, steroids, and the like.

Attachment of the antibody to the solid matrix material may be by absorption, or by covalent linkage, directly, or through a linker of sorts well-known to those skilled in the art. Suitable methods of carrying out these procedures among a wide variety, are given for example by Iman and Hornby in Biochemical Journal (Volume 129; Page 255; Campbell, Hornby, and Morris in Biochem. Biophys. Acta (1975), Volume 384; Page 307; and Mattisson and Nilsson in F.E.B.S. letters., (1977) Volume 104, Page 78. Moreover, chemically pretreated materials suitable for coupling antibodies can be purchased commercially.

Numerous materials can be utilized to fabricate support materials. Such materials are generally either synthetic or natural polymers examples of useful synthetic polymers being polyethylene, polyacrylamide, nylons resins, polyvinyl chloride, and polystyrene. Natural polymers typically used are cellulose, polysaccharides, Sepharose, agarose, and various dextrans. Additional material that can be employed to fabricate the support material are silica, particularly glass, collagen, and polynucleotides. While a variety of the materials described above will perform adequately in the subject invention, the preferred embodiment employs material composed of nylon.

An important aspect of the subject diagnostic device is the method of applying antibody to the solid matrix material 24. Most current methods non-selectively deposit antibody over the entire surface of the matrix material 24. This wastes antibody, which is often expensive or difficult to obtain, and, moreover, precludes assaying for more than one antigen present in the same sample. We have found that both problems are eliminated by spray delivering antibody in a thin fluid stream on to the matrix material 24. This is best achieved by forcing a solution containing antibody through a small bore nozzle whereupon the solution is fragmented into discrete droplets using sound vibrations or other means. The droplets are subsequently charged by passing through an electric field, and then deflected onto the matrix material 24. The procedures for effecting this method are described in U.S. Pat. Nos. 3,281,860 and 4,121,222, and are hereby incorporated by reference.

The above process is most readily achieved using a commercial printing device manufactured by Videojet Systems International. The device is termed a Videojet Coder/Printer, and provides a stream of antibody under a variety of conditions, and at varying stream widths. Using this device, it is possible to dispose a series of lines, or other patterns on the matrix material 24, each containing an antibody with different antigenic specificities.

It will be appreciated that spray application of antibody to the matrix material 24 is suitable either when antibody is sought to be associated with the matrix material 24 by simple absorption, or by covalent attachment with chemically pretreated matrix material.

FIG. 2 shows that situated beneath the solid matrix material, is a mid-layer of material 22. The mid-layer is situated between the absorbent material 20, and the matrix material 24, and acts to reduce the background of the assay. After the assay fluids pass through the matrix material 24, they contact, and filter through the mid-layer 22. The latter greatly reduces the background of the assay by reducing the backflow of unreacted reagents and thus keeps them from recontacting the matrix material 24. A wide variety of materials are suitable for forming the mid-layer 22. Particularly suitable is non woven polypropylene material commonly found in disposable diapers as described in U.S. Pat. Nos. 3,860,003, 4,081,301, and 4,515,595.

In addition to the mid-layer 22 another feature of the present diagnostic device which results in low background, and enhances its simplicity of use, is the filtering device 28 associated with the top section 12. It comprises a funnel shaped central region 38 that readily accommodates an amount of assay fluid needed to perform the assay in a single application, and a tab 34 that permits the user to grasp and remove the device 28. At the bottom of the filter device 28 is filter material 36. This material is impregnated with one or more reagents needed to perform the assay, and which are carried down onto the matrix material 24 with assay fluid when the latter is applied to the filtering device 28.

A variety of materials can be used to fabricate the filtering material 36 in the filtering device 28. Indeed,, for the most part those materials described supra that comprise the matrix material 24 can be suitably employed for the filtering material 36. We have found glass fiber is particularly suitable, an example being Ultipor GF Filter U6-40, from Pall Corporation.

A variety of reagents can be impregnated into, dusted onto, or otherwise associated with the filter material 36. It is particularly advantageous to have protein blocking agents associated with the filter material 36. The type of blocking agent is not critical. That is a variety of proteinaceous materials, amino acids, peptides can be suitably employed. However, we have found that milk protein is satisfactory, and routinely use non-fat dry milk sold by Carnation Corporation. Additional, in those instances when the solid matrix material 24 is chemically pretreated to covalently bind antibody, it may be desirable to use small molecular weight amino reactive reagents such as glycine as the blocking agent.

In order to effaciously associate blocking agent with the filter material 36, it is desirable to contact the filter material 36 with dry material for a time sufficient to uniformly coat the material. This can be accomplished by contacting the filter material with the blocking agent, followed by removing any material that is not firmly adherent to the filter.

It will be appreciated that an alternative method of associating the blocking agent with the filter material 36 is to contact the material with a solution containing the blocking agent, and then lyophilize the material. This is particularly useful when small molecular weight (i.e. glycine) blocking agents are used. While filter material so treated will perform adequately in the present device, it is not a preferred method because lyophilization causes the filter to harden which in turn increases the time it takes for solutions to pass through the filter material. This results in uneven deposition of the blocking agent on the matrix material 24, and an increase in background.

In addition to having blocking agents associated with the filter material 36 of the filtering device 28, it may also be desirable to impregnate other reagents into the material that are utilized in the assay, thereby avoiding having to add these reagents in separate steps. For example, it is anticipated that reagents used to reveal the presence of the antibody-antigen complex, that is antibody enzyme conjugates, or enzyme substrates, can be similarly associated with the filter material 36.

A second feature of the subject invention alluded to above, that is important in establishing the long term room temperature stability of the diagnostic device, is the utilization of a suitable chemical drying agent situated in chamber 18 in the bottom section 14. The stability, or useful lifetime, of the materials in the matrix material 24, or the filter material 36, is a function of the humidity encountered by the device. Presently used immunodiagnostic devices have a useful shelf time of less than 6 months at room temperature, whereas the present device has a room temperature shelf time of up to one year. We have found that by associating a drying agent with the diagnostic device that the reagents remain stable and give outstanding performance over this time. A variety of drying agents are well known in the art, and are anticipated to be useful.

In order to detect the presence of the immune complex on the matrix material 24, it is generally required that a labeled second detector molecule be used. In those instance where the complex is an immune complex, the detector molecule is a second antibody having specificity for antigen bound to the first antibody but binds to antigen at a site remote from that where the first antibody is bound. Traditional methods of detecting the presence of antigen have utilized a labeled second antibody wherein the label is often a radioactive tracer, or more recently an enzyme capable of hydrolyzing a colorless substrate to produce a detectable color changes thereby revealing the immune complex. A variety of enzymes are usable in combination with the appropriate substrate. For example horseradish peroxidase, beta-galactosidase, glucose oxidaser alkaline phosphatase, and others well known to those skilled in the art can be suitably employed. Most of these enzymes utilize diazonium or tetrazolium salts as substrates. Examples of the former are napthol AS MS phosphate and diazo 2-amino 5-chloro Anisol used as substrate for alkaline phosphatase.

Methods for associating enzymes with second antibody are well known to those skilled in the art, and primarily involve chemically coupling the enzyme to the antibody. Procedures for coupling antibody by chemical cross-linking are described by O'Sullivan and Marks in *Methods in Enzymology*, (1981) (73:147) Academic Pressp New York. If horseradish peroxidase is used then a suitable coupling method is that of Nakane and Kanaoi described in the *Journal of Histology and Cytochemistry*, (1974) (82:1084). This method effectively and directly conjugates the enzyme to the antibody; however other methods are well known, for example, an biotin-avidin bridge can be formed on the second antibody having horseradish peroxidase linked to avidin.

In lieu of chemically coupling the enzyme to the second antibody-enzyme conjugate, it may be preferred to have the enzyme integrated into the antibody. This can be accomplished, for example by genetically engineering hybrid molecules having both an antibody binding site, and an enzyme active site. For instance, antibody can be modified by DNA recombinant techniques as described by Neuberger et al in Recombinant Antibody Possessing Novel Efector Function, Nature (1984) (312:604). It is anticipated that this type of enzyme conjugate can be directly incorporated into the filtering material 36 of the filtering device 28r or can be added in a subsequent step to reveal the immune complex formed on the matrix material 24.

It will be appreciated by those skilled in the art that the antibodies that are deposited on the matrix material 24, or that comprise the antibody-enzyme conjugate, can be either monoclonal or polyclonal. After the antibody-enzyme conjugate has been added to the matrix material 24 and sufficient time has passed to maximize binding of the antibody-enzyme conjugate to bound antigen, a solution containing a suitable enzyme substrate is added, and the appearance of color is noted as being indicative of the presence of the antigen in the assay sample. In most instances, it will not be necessary to insert a wash step after the conjugate has been added, and before the addition of substrate. This is because the funnel shape of the aperture 26 enables a large amount of substrate solution to pass through a small amount of surface area of the substrate material. Thus, addition of the substrate solution in effect acts as a washing step. Nevertheless, however, for some applications it may be desirable to have a washing step to eliminate undesirable background.

The present invention will now be illustrated by the following examples. It will be apparent to those skilled in the art that there are a variety of substitutions possible for the material and methods employed. Consequently, the examples presented should be viewed as exemplary, and not as limiting the invention to the particular materials or methods described.

EXAMPLE 1

Detection of Chorionic Gonadotropin Hormone (hCG)

This example will be described with reference to FIGS. 1 and 2. An amount of urine corresponding to approximately 0.5 milliliters, and containing 25 mIU/ml hCG was applied to the filtering device 28. The urine contacts the filter material 36 of the filtering device 28, and passes through the filter material, carrying with it a protein blocking agent, milk protein, impregnated in the filter material 36. The filtrate containing the blocking agent passes through the aperture 26, present in the top 12 and contacts the matrix material 24. The matrix material 24 is impregnated with antibodies to human hCG. The matrix material was made of nylon, of a type well known and routinely used in the art.

Impregnation of the matrix material 24 was realized using a printer/coder machine as described in U.S. Pat. Nos. 3,281,860 and 4,121,222 by applying a narrow stream of fluid to the matrix material 24 containing mouse monoclonal antibody directed against the alpha chain of hCG. The antibody was applied in approximately 1.5 millimeter wide lines. For convenience to the ultimate user of the device, antibody was applied in a vertical line, that passed across a horizontal line of previously applied goat anti-mouse antibody of the IgG class. The latter will be explained in more detail infra. Application of antibody consists of spraying a solution containing 4 milligrams per milliliter of mouse monoclonal antibody against alpha chain of hCG in a suitable buffer, phosphate buffer saline is satisfactory. This consists of 10 mM sodium phosphate with 150 mM sodium chloride, pH 7.1. In addition, the solution contained 100 micro-grams per milliliter of flourescein, and a bacterial static agent such as, 0.1% sodium azide. Flourescein is applied to the solution to provide a visual means for assessing the pattern of antibody formed on the matrix material 24.

After the filtrate has passed through the filter material 36, it contacts the matrix material 24. hCG present in the filtrate binds to hCG antibody impregnated in the matrix material 24. In addition, simultaneously with this event, the blocking agent present in the filter 36 binds to the matrix material 24 at sites other than those to which the monoclonal antibody is bound. In so doing, these sites are made unavailable for reaction with subsequently added reactants. A short time after the filtrate contacts the matrix material 24, two drops of a solution containing a second mouse monoclonal antibody enzyme conjugate is added. The second antibody is directed against beta subunit of hCGp and binds to a different epitope than that to which the first antibody that is attached to the matrix material is bound. The enzyme component of the conjugate was alkaline phosphatase. The antibody-enzyme conjugate passes through the filter material 36, and contacts the matrix material 24 for a time sufficient for the conjugate to react and combine with hCG bound to the first antibody. Generally this takes about 1 minute.

In order to reveal the complex formed on the matrix material 24, a solution containing substrate for alkaline phosphatase, indoxyl phosphate, was added directly to the matrix material 24. In about 1 minute, a blue color formed on the matrix material 24, in a "+" pattern indicating that the assay sample contains hCG. Should a "−" sign appear,. the sample contains insignificant amounts of hCG. It is satisfactory if approximately 0.5 milliliters of the substrate solution containing 4 mM indoxyl phosphate is utilized.

Lastly, an amount of a suitable reaction stopping solution is added to the matrix material 24. 0.5 mls. of a solution containing 0.1 acetic acid performs satisfactorily.

The "+" pattern, as alluded to above, is realized by disposing anti-hCG first antibody in a vertical line over a horizontal line of either second antibody enzyme conjugate, enzyme alone, or goat anti-mouse antibody. The latter is preferred because it matches the type of reagent (i.e. protein antibody) used to form the vertical line of the "+" sign. Thus, any loss in activity over time in one reagent is balanced by a corresponding loss in the other. Regardless of which type of reagent is used to form the horizontal line, they can be applied by being sprayed onto the matrix material 24 as described above.

EXAMPLE 2

Room Temperature Stability

The materials and methods used in Example I can be similarly employed here. After storing a diagnostic device for one year at room temperature, it was successfully used to assay a sample containing 25 mIU/ml of hCG.

EXAMPLE 3

Antigen Impregnation of the Matrix Material

It will be apparent to those skilled in the art that the present diagnostic device is not limited to detecting antigens. It is equally possible to detect circulating antibodies present in the bodily fluids of a patient that has experienced a challenge to his immune system. This is done by attaching to the matrix material the antigen that is responsible for eliciting the immune response, and then assaying for the presence of antibody. This aspect of the diagnostic device is applicable, for example, in detecting or monitoring autoimmune, or allergy sufferers.

To demonstrate this aspect of the invention inactivated rubella virus can be attached to the matrix material 24 shown in FIG. 2, using a printer coder machine described in Example 1. Subsequently, a solution containing anti-virus antibody to be detected is added to the filtering device 28 shown in FIG. 2, and flows through the filter material 36, thereby producing a filtrate that passes through the aperture 26. The filtrate contacts the matrix material 24 containing bound virus. Anti-rubella virus antibody binds to the virus on the matrix, and the detection of anti-rubella antibody in the filtrate is then achieved by passing a solution containing antibody enzyme-conjugate, wherein the antibody is directed against bound anti-rubella antibody. The antibody component of the conjugate need only be capable of recognizing an epitope on the anti-rubella antibody to be effective. Assuming that the anti-rubella antibody being assayed is human, then the antibody component of the conjugate should be antihuman antibody. The remaining steps in this assay are analogous to those described in Example 1. The end result is the appearance of color on the matrix material 24 indicative of the presence of anti-rubella antibody in the assay fluid.

EXAMPLE 4

Impregnation of the Filter Material with Assay Reagents

One of the goals in diagnostic testing is to develop a test device that requires few manipulative steps. By associating assay reagents with the filter material 36 of the filter device 28, it is possible to eliminate those steps whereby the reagents are added separately to the matrix material 24 to carry out the assay.

Impregnation of the filter material 36 with proteinaceous blocking agents was achieved by pulverizing milk powder obtained from non-fat dry milk (Carnation Corporation), and sifted to remove any large granules still present. Next, the filter material made of glass fibers (pre-filter grade Ultipor GF Filter U6-40, Pall Corporation) was cut into two by two centimeter squares, and were stored in a closed container with a suitable drying agent. The papers were then mixed with pulverized milk powder for a time sufficient to impregnate the filters with milk powder, generally this requires approximately three hours. Uniform association of the milk powder with the filter was accomplished by tumbling, or otherwise agitating the filters while in contact with the powder.

Excess milk powder was removed from the filter squares by sifting through a flour sieve, and then the filter was transferred to a container where they were shaken for a time sufficient to remove any loose milk powder present. Generally, this requires about one hour. This step was followed by a second sifting step to remove any excess milk powder that was not earlier removed. The filters were stored in a container in the presence of a suitable drying agent. Filters prepared by this technique are directly usable in the diagnostic test device.

EXAMPLE 5

Detection of Multiple Antigens

The materials and methods described in this Example are similar to those of Example 1 with the following exceptions. The matrix material 24 is treated with 2 antibodies having distinct antigenic specificities, one directed against the beta subunit of luteinizing hormone (LH) and the other against the beta subunit of follicle stimulating hormone (FSH). Using a printer coder machine described in Example 1, the antibodies can be deposited in discrete patterns on the matrix material 24. The second antibody that comprises the antibody enzyme-conjugate for detection of either LH or FSH can be either a single monoclonal antibody that recognizes a common epitope on LH and FSH, or two monoclonal antibodies that bind to different epitopes on LH and FSH. In the latter case, two different enzymes that yield distinct color reactions can be bound to the monoclonal antibodies to produce distinct colored "+" signs. For example, alkaline phosphatase, and B-galactosidase can be used, the former gives a red color with a proper substrate, and the latter a blue color.

Lastly, the horizontal line component of the "+" sign for LH and FSH can be formed as described in Example I.

EXAMPLE 6

Sensitivity of the Diagnostic Device

The materials and methods described in Example 1 are employed here to compare the sensitivity and time of performance of the present device with presently used commercial devices. For each of the commercial devices the manufacturers procedures were followed. Solutions containing varying amounts of hCG were tested and table 2 shows the detectable lower limit, or sensitivity of the devices. Also shown in the table is the method on which the assay is premised, types of antibodies, and the time it takes to perform the assay.

The invention described above has been described with respect to the use of specific materials and methods. However, it will be apparent to those skilled in the art that the invention is not so limited. Indeed, it is readily apparent that there exists numerous equivalent materials and methods that may be resorted to without departing from the spirit and scope of the invention.

TABLE 1

| | |
|---|---|
| ICON (Hybritech, Inc.), hCG | Kit requires storage at 2–8 C. |
| TEST PACK (Abbott Labs, Inc.), hCG | Antibody Enzyme Conjugate should be stored at 2–8 C. |
| RAMP (Monoclonal Antibodes, Inc.), hCG | Kit should be kept at 2–8 C. |

TABLE 2

| DIAGNOSTIC DEVICES | METHOD | SOURCE OF ANTIBODY | REACTION TIME | SENSITIVITY |
|---|---|---|---|---|
| Present Device | EIA, Coated Membrane | Mouse Monoclone | 2 Min. | 20 mIU/ml (1st IRP) |
| TEST PACK hCG-URINE Abbott Laboratories | EIA, Coated Filter | Mouse Monoclone | 3 Min. | 50 mIU/ml (1st IRP) |
| ICON® HCG-Urine Hybritech | EIA, Coated Membrane | Mouse Monoclone | 3 Min. | 50 mIU/ml (1st IRP) |
| TANDEM Visual HCG (Urine) Hybritech | EIA, Coated Bead | Mouse Monoclone | 45 Min. | 50 mIU/ml (1st IRP) |
| RAMP™ Urine hCG Assay Monoclonal Antibodies, Inc. | EIA, Coated Membrane | Mouse Monoclone | 3 Min. | 50 mIU/ml (1st IRP) |
| DUOCLONE™ Slide Organon | Latex Agglutination | Mouse Monoclone | 3 Min. | 500 mIU/ml (2nd I.S.) |
| BETA Quik Stat Pacific Biotech, Inc. | EIA, Coated Tube | Mouse Monoclone | 5 Min. | 25 mIU/ml (2nd I.S.) |

We claim:

1. In an immunoassay device having a housing with at least one opening therethrough for introduction of a liquid sample into the housing, a web of porous material in said housing adapted to be contacted by said liquid sample, and at least one immunological reagent in dried form on said web, the improvement comprising:

a desiccant material in said housing, wherein said desiccant is capable of retarding deterioration of said reagent.

* * * * *